United States Patent
Tavares et al.

(10) Patent No.: US 7,150,775 B2
(45) Date of Patent: Dec. 19, 2006

(54) POWDER METAL MIXTURE INCLUDING MICRONIZED CELLULOSE FIBERS

(75) Inventors: Bruce Anthony Tavares, Hartland, WI (US); Bart Jerome Nelson, Johnsonburg, PA (US)

(73) Assignee: React-NTI, LLC, Lino Lakes, MN (US)

( * ) Notice: Subject to any disclaimer, the term of this patent is extended or adjusted under 35 U.S.C. 154(b) by 156 days.

(21) Appl. No.: 10/758,032

(22) Filed: Jan. 14, 2004

(65) Prior Publication Data

US 2004/0144207 A1    Jul. 29, 2004

Related U.S. Application Data

(63) Continuation-in-part of application No. 10/229,452, filed on Aug. 28, 2002, now Pat. No. 6,683,031, which is a continuation-in-part of application No. 09/961,842, filed on May 21, 2001, now Pat. No. 6,506,712.

(51) Int. Cl.
  *B22F 1/00*   (2006.01)
  *C08L 1/02*   (2006.01)
  *B22F 3/00*   (2006.01)

(52) U.S. Cl. .......................... 75/252; 524/35

(58) Field of Classification Search ................ 75/252; 524/35

See application file for complete search history.

(56) References Cited

U.S. PATENT DOCUMENTS

| | | |
|---|---|---|
| 4,886,637 A | 12/1989 | Jadeska, Jr. et al. |
| 5,480,469 A | 1/1996 | Storstrom et al. |
| 6,413,919 B1 | 7/2002 | Vidarsson |
| 6,511,945 B1 | 1/2003 | Ramstedt |
| 6,573,225 B1 | 6/2003 | Vidarsson et al. |

OTHER PUBLICATIONS

Jones, L.D., et al.; The Effect of Microcrystalline Cellulose on the Mixing and Compaction Response of Ferrous Powders. 1981, Powder Technology, 30(1), 9-19.*

* cited by examiner

*Primary Examiner*—Ngoclan T. Mai
(74) *Attorney, Agent, or Firm*—Alfred D. Lobo

(57) ABSTRACT

A powder metal mixture comprises a lubricant powder conventionally used to produce powder metal parts in combination with micronized cellulose fibers in an amount less than 2% by weight of the mixture. The addition of fibers with the lubricant increases green strength of a part made by compacting the mixture and improves dimensional conformance.

7 Claims, No Drawings

POWDER METAL MIXTURE INCLUDING MICRONIZED CELLULOSE FIBERS

CROSS REFERENCE TO RELATED APPLICATIONS

This patent application is a continuation-in-part application of Ser. No. 10/229,452 filed 28 Aug. 2002 now U.S. Pat. No. 6,683,031 which is a continuation-in-part application of Ser. No. 09/961,842 filed 21 May 2001, issued as U.S. Pat. No. 6,506,712 ("'712 patent") on 14 Jan. 2003.

FIELD OF THE INVENTION

The present invention relates to a novel powder metal mixture in which a particulate ferrous metal powder in combination with a binder and lubricant is conventionally molded into an article of arbitrary shape and size having sufficient green strength to be ejected from the die in which the article is molded without scoring the die and without generating so much heat as to blister lubricant out of the compacted part.

BACKGROUND OF THE INVENTION

The demands of mass production of metal parts for appliances, vehicles and machines of all types has driven the technology of powder metallurgy ever since it was discovered that a mixture of the appropriate finely divided metal particles in the form of a powder, mixed with a binder and lubricant, each also in finely divided form, could be compacted and sintered to yield an article of arbitrary shape and size. In the art, "powder metal mixture" refers to a mass of particles each of which is less than 150 μm (micrometers or microns) in average equivalent diameter ("avg. equiv. dia."), preferably its largest dimension, the metal particles typically being largest, preferably having an avg. equiv. dia. of less than 75 μm, the smallest metal particles having an avg. equiv. dia. of about 25 μm, and the non-metallic additives typically having an avg. equiv. dia. less than 50 μm. Because powder metal particles may be irregular in shape, the equivalent diameter of a particle refers to its diameter had it been a sphere of equal volume. Depending upon the physical properties demanded of the sintered or sintered and heat treated ferrous article, a wide array of powder additives are added. The most common of such additives are a lubricant and/or binder followed by graphite and metals such as nickel, copper, molybdenum, manganese, chromium, cobalt and/or an organometal or metal compounds such as sulfides, phosphides, and the like which become alloyed with the powder metal when sintered and/or heat treated. The term "powder metal mixture" in this invention refers to a mixture of ferrous metal particles in which iron (Fe) is present in an amount greater than 90 per cent, the remaining ingredients being additives such as a lubricant, optionally a binder which may be the same as the lubricant or different, and alloying ingredients such as graphite and metals, each present in an amount less than 2 per cent by weight (% by wt) of the total mixture including the powder. The term "lubricant" refers to a powder of particles no dimension of which is more than about 100 μm, and typically having an avg. equiv. dia. in the range from about 5 μm to 25 μm; in this invention the lubricant is modified to consist essentially of a lubricant powder such as is conventionally used to make a compact mass of powder metal, blended with fragmented cellulose fibers having an average length less than 150 μm, preferably less than 20 μm, and a diameter in the range from about 1 μm to 20 μm.

The overriding criterion for a practical powder mixture is its homogeneity without which there would be an unacceptable variance in composition of a compacted metal part, not only from part to part, but within a part itself. The term "part" is used interchangeably with the more formal term "article". Such homogeneity encompasses not only the distribution of particles within a mass of unit volume of powder but the bulk density (measured as "Hall apparent density") and flow characteristics (measured as "Hall flow rate") of the powder mixture. The apparent density is the mass of a unit volume of non-compacted powder. Hall apparent density is measured as set forth in ASTM B-212 (Metal Powder Industries Federation "MPIF" test method 04 in "Standard Test Methods for Metal Powders and Powder Metallurgical Products). The flow rate is quantified as the time required for a powder of standard weight to flow through a Hall flow meter. The Hall flow rate is dictated by ASTM B-213 (MPIF test method 03). A variation in bulk density and flow will result in a variation in the "fill", which is the amount of powder mixture filled in a die cavity before the mixture is compacted, and the dimensions of the compacted part. To a lesser extent, a lack of homogeneity is reflected in variations in green strength of a compacted part particularly in sensitive portions of the molded part, such as the teeth of a gear.

Mainly because adequate green strength is obtained by increasing compacting pressure, green strength as a serious problem attracts attention only in those instances where compaction, or molding pressure is already so high as to shorten the useful life of a die noticeably and/or a worrisome number of compacted parts are damaged when being ejected from the die, or being automatically conveyed to a sintering oven under conditions which cannot preclude the green compacts from being impacted, even if not forcefully.

Green strength is measured as pressure required to break an unsintered compact (a standard rectangular bar) as set forth in ASTM B-312 (MPIF test method 15).

Though the terms "binder" and "lubricant" are used as if to specify different functions in a powder metal blend to be compacted, in practice, the same function may be discharged by a single ingredient, though each function may be to a greater or lesser extent than when discharged by different highly specialized materials. In particular, ethylene-bis-stearamide ("EBS") is sometimes referred to as a "binder" though it may also function as a lubricant, and metal soaps and waxes are typically referred to as "lubricants" though they may also function as binders. The term "blend" refers to a ferrous metal powder including all ingredients essentially homogeneously dispersed and in condition to be compacted. By "ferrous" metal powder is meant one in which the metal particles contain predominantly the element iron (Fe), typically at least 75% Fe. The binder binds particles of graphite and alloying components to the surface of metal particles. The lubricant reduces friction generated when the powder is subjected to shear, or, stressed; thus, metal powder with lubricant particles flows more easily than without the lubricant; and, a powder mixture with lubricant added to the metal particles may be compacted in a die under pressure and, if the compact has sufficient green strength, ejected from the die with less wear and tear on the die parts.

Typically, the green article is then sintered. The strength of the sintered bar is measured as "transverse rupture strength" ("TRS") using a standard TRS fixture as described in ASTM B-528 (MPIF test method 41). If the TRS is satisfactory, the tensile strength will generally be satisfactory. Depending upon the composition of the mixture of powder metal and additives from which the article is molded, and its end use, it may be subjected to further processing steps such as sizing/coining, resintering, heat treating, and others.

Recognizing that the component powders of metal, binder and/or lubricant and one or more additional additives differ in size, density and shape, the problem of homogeneity is minimized by choosing particles of comparable size and shape and thoroughly mixing the various particles before using the powder mixture. In this framework it is evident that any thought of mixing an organic fiber of vegetable material with the other particles, no matter how beneficial the fiber might otherwise be, will be quickly dispelled.

Moreover, to date, comminuted cellulose fibers have been available in an average length no shorter than 70 µm because attempting to comminute them further typically results in forming a fibrous compacted matte. Though the length of such comminuted fibers is in the same size range as the average equivalent diameter of metal particles used in a compactable powder mixture, addition of such fibers in an amount as little as 2% by weight of the total powder mixture, results in unacceptable bulk or apparent density and flow characteristics if the mixture is to be used in the mass production of compacted and sintered parts. The poor physical properties of a powder metal mixture containing fibers 150 µm and longer is attributable to the volume the fibers occupy and the irregularity of their individual shapes.

On the other hand, it is well recognized that the increased surface area contributed by the smaller particles in a powder mixture relative to the area contributed by the larger ones, impairs the "flowability" or flow characteristics of the powder mixture, resulting in a longer time required to fill a die and additional risk of non-homogeneity in compacted parts. Though such flowability is not a problem when compacting a dozen parts or so in a laboratory, the problem may be critical in a production facility where the number of parts which can be produced per unit time is a deciding factor.

Another serious problem which has loomed large in recent years is the extent of "dusting", particularly of graphite, and the harmful side effects of vaporizing zinc stearate, commonly used as a lubricant, during sintering. To cope with the latter problem, particularly having to clean sintering furnaces and their flues, the art is proliferated with disclosures of numerous other lubricants including waxes and metal soaps. To minimize or eliminate the use of zinc stearate, polyethylene oxide in combination with an oligomeric amide is disclosed in U.S. Pat. No. 6,511,945; and EBS or a polycarboxylic acid amide wax is used as a binder, but making a homogeneous powder mixture typically requires heating the wax to distribute it uniformly as a coating on the metal particles, as disclosed in U.S. Pat. No 5,480,469 to Storstrom et al. and U.S. Pat. No 6,573,225 to Vidarsson et al. respectively. To improve lubrication, U.S. Pat. No. 6,413,919 uses a combination of two well-known lubricants, each effective in its own right, one a fatty acid mono- or bis-amide, e.g. EBS, the other a metal soap, e.g. zinc stearate, and relies upon processing the mixture to form a core of one lubricant coated with the other. Though cellulose derivatives are broadly suggested as binders (see U.S. Pat. No. 5,480,469) and cellulose ester resins and hydroxyalkyl cellulose resins have also been suggested (see U.S. Pat. No. 6,573,225) it is evident that these compounds are physically and unrelated to cellulose fibers and have no analogous chemical properties.

SUMMARY OF THE INVENTION

An article of arbitrary shape and size is provided which is molded from (i) a ferrous metal powder having an average particle size smaller than about 150 µm (30 mesh U.S. Standard Sieve Series) in combination with (ii) a particulate, flowable lubricant having an average particle size smaller than about 50 µm, preferably smaller than 30 µm, and with (iii) fibers of cellulose, exemplified by fibers of natural cotton, the seed hairs from Gossypium, having a length in the range from about 1 cm–2 cm and a diameter in the range from about 5–20 µm, which have been fragmented into micron-sized portions ("micronized") of fibers having an average length smaller than 70 µm, preferably smaller than 30 µm; the article is molded from a powder metal mixture in which the lubricant and micronized fibers are together present in an amount in the range from about 0.01% to less than 2% by wt, each preferably present in an amount less than 1% by wt of the mixture. Though the diameter of the majority of the fibers is not diminished by comminution, a substantial number of fiber fragments, in the range from 5 to 40% by wt have an average length in the range from 2 to 20 µm, and from 1 to 20% by wt have an average length in the range from 1 to 10 µm and an average diameter in the range from 0.5 to 5 µm. Preferably, after being micronized, 90% of the fibers are smaller than 25 µm, most preferably smaller than 10 µm, having a median value in the range from about 8–12 µm and a mean value in the range from about 9–15 µm, as measured in a Microtrac Standard Range Particle Analyzer.

In view of the reliance (in the aforementioned '919 patent) upon the inherent well-known lubricity of a wax and/or a metal soap, in combination with the known spherical shape of atomized lubricants to provide highest flow rate and apparent density, it is particularly unexpected that fragmented fibers of cellulose, a material which has no lubricity and low apparent density, could be combined with a known lubricant and yield a fiber-modified lubricant, referred to herein as "modified lubricant" or more conveniently as "fiberlube", which not only has essentially the same physical properties of the lubricant without the fibers, but also results in a blend with substantially similar apparent density and a compact with better green strength.

Though micronized cellulose fibers (derived by fragmenting longer fibers) in the size range and amount specified above, by themselves, contribute no evident lubricity to a powder metal blend, they may be used in combination with any lubricant suitable for providing a compactable powder metal mixture, whether of low alloy steel or stainless steel, or prealloyed iron powder; preferably the ratio of cellulose fibers to lubricant is adjusted to provide a "modified lubricant" or "fiberlube" which, blended with powder metal, yields a blend which has specifications of Hall apparent density and rate of flow dictated by the production requirements of a die for a chosen green part. A green part compacted with the fiberlube provides higher green strength than another part compacted with the same lubricant (present in the same amount as the fiberlube but without the fibers) under the same conditions, while meeting predetermined specifications of hardness and TRS for sintered parts. By "low alloy" powder is meant an iron-based powder which may contain from 0.5% to 5% by weight of graphite and from 0.1% to 25% of an element selected from the group consisting of Ni, Cu, Cr, Mo, Mn, P, Si, V and W. By "stainless steel" is meant a corrosion-resistant steel of a wide variety of compositions, but always containing a high percentage of chromium in the range from about 8% to 25%, typically from 0 to 12% Ni, and from 0 to about 0.5% C (carbon). By "prealloyed" is meant that the iron is melt-processed in such a manner as to have substantially homogeneously intermixed with it one or more alloying elements. Low alloy steel parts are typically made with much smaller amounts of other elements than either chromium or nickel, copper being used in a higher amount, up to about 5%, than Mn, Mo, Si, V, P and W which are typically used in an amount less than about 2%.

A ferrous metal powder may be selected from any of the foregoing iron-based powders. Typically, the ferrous metal powder is atomized powder or derived from a sponge iron with particles in a size range chosen to meet the specifications of the sintered final product. Though any conventionally used waxy lubricant may be used, e.g. EBS, a preferred lubricant is a micronized polyolefin wax commercially available as a polymerized lower olefin oxide, or an oxidized polyolefin homopolymer or copolymer, the olefin having from 2 to 4 carbon atoms; most preferred is an oxidized micronized polyolefin homopolymer wax. Since less than 0.1% by weight of the fibers does not contribute appreciable advantage over the lubricant by itself, the amount of fiber-lube used is preferably in the range from 0.25% to 1% by weight and the weight ratio of lubricant/fibers is in the range from about 1:2 to 10:1, preferably from 1:1 to 4:1.

A method is disclosed for making a homogeneous powder metal mixture comprising, mixing metal particles having an average equivalent particle diameter smaller than about 150 µm with additives including a modified lubricant present in an amount less than 2% by wt of the mixture, and optionally a binder, processing aids and additives conventionally used in the art, the modified lubricant consisting essentially of a lubricant preferably having an average equivalent particle diameter smaller than 50 µm, in combination with cellulose fibers having an average length smaller than 70 µm, for a time sufficient to yield specifications of (i) Hall apparent density numerically no smaller than 10% less than that obtained for the same powder metal mixture made with a conventional lubricant without the cellulose fibers, and (ii) Hall flow rate which is at least 25 sec/50 g of mixture. Preferably, the Hall apparent density is numerically greater than that obtained for the same powder metal mixture made with a conventional lubricant without the cellulose fibers.

In a powder metal mixture made with less than 2% by wt of a conventional lubricant, which mixture has an unacceptably low Hall flow rate of less than 25 sec/50 g, the addition of an equal part by weight but at least 0.1% by weight of micronized cellulose fibers which, by themselves provide a mixture of negligible lubricity, so that the fibers and lubricant are together present in an amount less than 2% by wt of the mixture, yields a blend which not only has desirable Hall apparent density and flow rate but also results in higher green strength than if the cellulose fibers were omitted. A commercially usable blend of ferrous powder metal including less than 2% by wt of modified lubricant including from 0.1% to less than 1% by wt of micronized cellulose fibers in combination with from 0.1% to less than 1% by weight of a conventional, preferably polymeric lubricant has a Hall apparent density in the range from 2.7 to 3.5 g/cc, preferably from 2.9 to 3.3 g/cc and a Hall flow rate in the range from 25–35 sec/50 g, preferably from 29–33 sec/50 g. Blends which flow too slowly, or not at all, usually flow through a powder bin's delivery tube with no difficulty; such minor difficulty in filling a die cavity as may be encountered with some weight ratios of fibers/lubricant, may be overcome using an agitation means on the delivery tube, such as a mechanical or sonic vibrator. The slightly lower apparent density typically obtained with the novel modified lubricant is compensated for by deepening a die cavity conventionally used with a blend having a higher apparent density.

Micronized cellulose fibers as defined herein, in combination with a micronized polyolefin wax particles having an equivalent diameter smaller than about 50 µm, are ingredients of a novel composition found not only to be a substitute for a metal soap such as zinc stearate or a fatty acid mono- or bis-amide, either wholly or in part, but also to provide higher green strength than is obtainable with an equivalent weight of lubricant without the cellulose fibers. When molded green ferrous powder metal articles containing the modified lubricant are sintered in an oxygen-free atmosphere of a conventional sintering oven, the oven's flue does not require frequent cleaning as is the case with sintered zinc stearate-containing articles. The micronized fibers may also be combined with an inorganic lubricant such as graphite, the function of the fibers being, in part, to replace a portion of the graphite otherwise used, or be combined with an organometal such as zinc stearate, the function of the fibers being, in part, to replace a portion of the organometal otherwise used.

DETAILED DESCRIPTION OF THE INVENTION

It is critical that micronized cellulose fibers be used. By cellulose fibers we refer to fibers of a predominantly cellulose material such as hemp, jute, cotton, wood, sisal, bamboo, corn stalks and the like which yield individual fibers having a diameter less than about 20 µm. Though any of such cellulose fibers may be comminuted to an average length less than about 75 µm, they are more easily micronized into fragments in the smaller size range after they are subjected to gamma ray, X-ray or electron beam radiation in an amount sufficient to render the exposed fibers highly frangible, as disclosed in the aforementioned '712 patent the disclosure of which is incorporated by reference thereto as if fully set forth herein. It is believed that when a dosage in the range from 30 to 100 MR (megaRads) is delivered to a mass of cellulose fibers their surface structure is also modified in such a way as to facilitate flow of a powder metal mixture when exposed comminuted fibers are mixed with comparably small or smaller particles of conventional organic lubricants. Most preferred are cellulose fibers which may be bleached without altering their molecular structure. It is recognized that the diameter of each fiber gets thicker as layers of cellulose build up on cell walls of the fiber over the time of growth of the raw material from which the cellulose is harvested; it is desirable to use raw fibers having an average diameter such that upon comminuting the fibers, at least 50% by weight have an average length less than 70 µm and a diameter less than 10 µm. By "raw material" is meant that the fibers are not chemically processed to alter the structure of the cellulose molecules, that is, the unique structure of cellulose or polycellobiose relative to other polysaccharides is maintained and not derivatized. Most preferred are cellulose fibers which have been subjected to irradiation by an electron beam in the aforementioned dosage range, the fibers thereafter being comminuted, in a high-speed rotary cutter such as a Model 811 Series Inline Granulator, or in a jet classifying mill such as a Model 30 Roto-Jet, or a Model 24, having an average length in the range from about 1 to less than 50 µm, and an average diameter in the range from about 1 to 10 µm, preferably from about 1 to 20 µm in average length and from about 1 to 5 µm in average diameter, and most preferably from about 1 to 10

μm in average length and from about 1 to 3 μm in average diameter. These dimensions, in the smaller size range, of such comminuted electron-beam irradiated fibers depends upon in large part upon the source of the cellulose fibers and the dimensions of individual fibers before they are comminuted, and the degree of impact between fibers themselves while they are being comminuted.

Any conventional powder metal lubricant may be used in the powder metal mixture, and particularly favored lubricants are those which imbue the blend with a Hall apparent density in the range from 2.7–3.5 g/cc and a Hall flow rate in the range from 29–35 sec/50 g. Commonly used lubricants are selected from the group consisting of metal soaps, and waxes particularly poly (lower)olefin waxes and oxidized poly(lower)olefin homopolymers and copolymers, fatty acid bis-amides and fatty acid mono-amides. Preferred waxes are the Epolene® brand waxes designated E-10, 14, 15, 16, 17, 20, 43; G-3003 and G-3015; E-14, 20, 43; C-10, 13, 16, 17, 18; N-10, 11, 14, 15, 20, 21, 30, 34, 3; commercially available from Eastman Chemical Co.; and the Acumist® brand waxes designated A-6, 12, 18, 45; B-6, 9, 12, 18; C-5, 12, 18; D-5, 9; 1106, 1112, 1204, 1306, 3105, 3205; commercially available from Honeywell Corporation. The particular choice of wax will depend upon the physical characteristics of a particular metal powder, the conditions under which it is to be compacted and ejected, and the conditions under which the compacted part is to be sintered.

A blend containing a lubricant in combination with micronized cellulose fibers is conventionally prepared, requiring no additional processing steps. The ingredients are mixed until an essentially homogeneous blend is formed, and a die cavity in which a part is to be molded is filled with the blend; the blend is then compacted with a ram, matingly closely fitted into the die cavity, which exerts sufficient pressure, typically in the range from about 300 to 900 Mpa (43,500 psi or 43.5 Ksi or 21.75 Tsi, tons/in$^2$) to 1000 Mpa (130,500 psi or 130.5 Ksi, or 65.25 Tsi) to form a green part; the green part is then ejected from the mold with a peak ejection force insufficient to damage the integrity of the molded part, the force being in the range from about 453.6 to 2041.2 Kgf, kilograms-force (1,000 to 4,500 lbf, pounds-force). The green part is then sintered in a sintering furnace in an inert atmosphere, typically nitrogen and/or hydrogen, under elevated temperature conditions high enough to volatilize the lubricant and some or all of the cellulose fibers, and form a sintered metal part. The furnace encloses a belt moving at a speed sufficient to provide the desired time in the furnace's hot atmosphere, typically of 80% $N_2$/20% $H_2$, the belt speed being in the range from 2.54 cm (1") per min to 30.5 cm (12") per min in zones ranging from about 1000° F. to 2500° F.

Low alloy and prealloyed parts are typically not heat treated unless they contain enough graphite to warrant heat treating. Stainless steel parts are not heat treated. In most of the illustrative examples presented below, cellulose fibers having an average length less than 10 μm and an average diameter less than about 5 μm are used to avoid having the dimensions of the fibers interject an additional variable. The apparent density and flow rate of a blend containing only the cellulose fibers and no lubricant were not measured because when a blend containing 0.75% by weight of cotton fibers was compacted with a pressure of 7030.77 Kg/cm$^2$ (50 TSI), the bar could not be ejected from the die cavity with an acceptable amount of force, indicating that cellulose fibers provided no evident lubricity; therefore, a blend with fibers and no lubricant would not be usable. Further, only the essential ingredients are used to make each blend so as to focus the result-effectiveness of the cellulose fibers. To focus the effect of cellulose fibers in all blends, use of graphite is avoided unless the graphite is necessary to provide the desired properties of the sintered part.

EXAMPLES

The present invention is further illustrated by the following examples wherein the term parts refers to parts by weight unless otherwise indicated. All results are the average of a statistically significant number of identically performed tests, typically at least three. The following examples are not meant to be limiting, rather they are illustrative of only a few embodiments within the scope of the present invention.

Examples 1–7

Evaluation of Hall Apparent Density and Hall Flow Rate for MPIF F-0000 compositions using Hoeganaes Ancorsteel 1000B as the base iron and various lubricants, some in combination with cotton fibers, each lubricant or combination in an amount of 0.75% by weight (of the total mixture):

In the following Table 1, each sample is prepared as a 1 lb powder metal mixture ("end") which was blended by thoroughly mixing the ingredients in a cylinder about 8 cm (3 ins) in diameter and about 30.5 cm (12") long. The cylinder is manually rolled for 30 sec, that is, it is rotated about its longitudinal central axis while being translated back and forth on a table; the cylinder is then tumbled, end over end, for 30 sec, that is, it is rotated end over end about its central lateral axis; then the cylinder is shaken by hand in plural axes for 30 sec. This procedure carried out over about 90 sec is then repeated once more to ensure substantial homogeneity. Each blend is then evaluated for Hall apparent density. The lubricant, P-105 (internal code designation) is a commercially available micronized Acumist® polyolefin wax having a melting point in the range from about 137° C.–138° C. (279° F.–281° F.) which wax is used by itself in Blend 1, and in Blends 2, 3 and 4 in combination with different proportions of micronized cotton fibers. In Blends 5 and 6 the widely used lubricants zinc stearate and EBS are used, each by itself; and in Blend 7, 0.56% fibers are combined with 0.19% EBS, the same proportions used with the polyolefin wax in Blend 3.

TABLE 1

| Blend No. | Lubricant Type % lubricant/% fibers | Hall Apparent Density g/cc | Hall Flow Rate sec/50 g |
|---|---|---|---|
| 1 | 0.75% P-105 | 3.00 | No Flow* |
| 2 | 0.38% P-105/0.38% fibers | 3.05 | 30 |
| 3 | 0.56% P-105/0.19% fibers | 3.07 | 35 |
| 4 | 0.19% P-105/0.56% fibers | 3.04 | 29 |
| 5 | 0.75% zinc stearate | 3.23 | 28 |
| 6 | 0.75% EBS (Acrawax ®) | 2.99 | 28 |
| 7 | 0.19% EBS/0.56% fibers | 3.16 | 31 |

*the powder does not flow through the funnel unless agitated

It is evident from the foregoing data that the micronized polyolefin wax, used by itself, is of no practical use as the blend does not flow. The remaining blends meet the accepted criteria for Hall apparent density and flow rate which are desirably in the ranges from 2.9 to 3.3 g/cc and 27 to 36 sec/50 g respectively. Compared to EBS and zinc stearate, blends with cotton fibers have a Hall apparent density between that of EBS and zinc stearate; and better Hall flow rate than either; blends #4 and #7 with the same proportion of cotton fibers have substantially the same apparent density and flow rate whether the lubricant is EBS or polyolefin wax, indicating substantially no sensitivity to the choice of a conventional, good lubricant.

Note however, that the blend with 0.75% P-105 lubricant which does not flow readily through the funnel, has an apparent density of 3.00 g/cc, which is essentially the same as the apparent density with an equivalent amount of EBS; however, though the apparent density of fragmented cellulose fibers is much lower than that of metal powder, in each case where a portion of the P-105 is substituted with cotton fibers, the apparent density unexpectedly increases; and this hot atmosphere of 97% $N_2$/3% $H_2$, the belt speed being in the range from 2.54 cm (1")/min to 30.5 cm (12")/min through four main temperature zones at 648.9° C. (1200° F.); 760° C. (1400° F.); 1121° C. (2050° F.); and 1121° C. (2050° F.) The length of each zone is approximately 3 meters (7' 7").

The sintered density, sintered TRS, sintered apparent Rockwell F hardness (HRF), and sintered dimensional conformance (DC) of at least three samples are measured and averaged. The results are presented in the following Table 2:

TABLE 2

| Blend No. | Green Density g/cc @ 7+K Kg/cm² | Green Strength MPa (psi) @ 7+K Kg/cm² | Peak Ejection Pressure Kgf (lbf) @ 7+K Kg/cm² | Sintered Density, g/cc | Sintered TRS MPa (Ksi) | Sintered Apparent Hardness H RF | Sintered DC, % from Die Size |
|---|---|---|---|---|---|---|---|
| 1 | 7.15 | 25 (3625) | 1406 (3100) | 7.07 | 358 (52.) | 60 | 0.31 |
| 2 | 7.16 | 19.08 (2769) | 1496 (3300) | 7.16 | 503 (73.) | 58 | 0.16 |
| 3 | 7.15 | 19.55 (2838) | 1315 (2900) | 7.12 | 406 (59.) | 60 | 0.25 |
| 4 | 7.13 | 24.89 (3613) | 1587 (3500) | 7.14 | 620 (90.) | 71 | 0.09 |
| 5 | 7.18 | 13.12 (1908) | 1542 (3400) | 7.14 | 509 (74.) | 69 | 0.28 |
| 6 | 7.19 | 14.51 (2107) | 1406 (3100) | 7.17 | 585 (85.) | 71 | 0.23 |
| 7 | 7.12 | 15.95 (2315) | 1723 (3800) | 7.15 | 661 (96.) | 79 | 0.10 |

In the above Table 7+K Kg/cm² refers to 7,030.8 Kg/cm² pressure = 50 tons/in² (TSI), and, Mpa refers to megapascals where 1 Mpa = 1000 KPa increase is also evident when a portion of the EBS is substituted with cotton fibers. Clearly, addition of fiberlube in an amount in the range from 0.25% to 1% by weight, to fast-flowing powders having a flow rate greater than 35 sec/50 g will have a negligible effect on flow and not adversely affect it, but one would not expect addition of fiberlube to Ancorsteel 1000B metal powder having a flow rate of 30 sec/50 g to improve the flow rate; nor would one expect the addition to increase apparent density of the blend.

Each blend was then compacted at 7030.77 Kg/cm² or 50 TSI (tons/sq inch) into standard test bars, each 3.175 cm (1.25") long×1.27 cm (0.5") wide ×0.635 cm (0.25") thick, to evaluate the effect of each lubricant on compressibility and green strength. Thereafter all the bars are sintered on a moving belt in a conventional sintering furnace at 1121° C. (2050° F.) in a 80% nitrogen/20% hydrogen atmosphere and properties of the sintered bars are evaluated.

It will be appreciated that the combined amount of lubricant and fibers used, as well as the ratio of fibers to lubricant, will depend upon the particular powder metal mixture being compacted, and the specifications (to be met) of the sintered part. Too high or too low a combined amount, or ratio of one component relative to the other, will result in a blend which is outside the desirable parameters of apparent density and flow rate. In general, when the combined amount is less than 0.5% or more than 1.5% by weight, the blend is not readily usable in a production run; therefore the combined amount is preferably no more than 1.5% by weight, and more preferably no more than 1% by weight.

The bars made with the blends numerically identified in Table 1 above are evaluated for green density, green strength, and the peak ejection pressure required to eject the bars from the die cavity. The bars are then sintered in a sintering furnace equipped with a belt moving at 8.9 cm (3.5") per sec through zones having successively higher temperatures of to provide the desired time in the furnace's It is evident from the foregoing results that Blend #4 in which the combination includes a major proportion by weight of cotton fibers relative to the amount of lubricant, provides sintered bars having not only the highest green strength, TRS and hardness (HRF) but also the best dimensional conformance (DC), that is, the least distortion.

Compared to EBS and zinc stearate, blends with cotton fibers, the green bars have a similar green density, and desirable peak ejection pressure (measured with a load cell).

Examples 8–11

Evaluation of a fiberlube which is a combination of 50% micronized polyolefin wax lubricant ("wax") and 50% micronized cotton fibers, together present in 0.75% by weight in two standard powder metal compositions:

To compare the effect of the fiberlube to the effect of a conventional, atomized Acrawax® EBS lubricant in (i) a MPIF F-0000 iron powder metal, and, (ii) a MPIF FC-0208 powder metal, four blends are prepared. For MPIF F-0000 we use Hoeganes Ancorsteel 1000 Base Iron; and for MPIF FC-0208 we use (Hoeganes Ancorsteel 1000 Base Iron+2% Copper+0.8% Graphite).

First, two lots are homogenized in a laboratory double cone blender with separate lots of MPIF F-0000 and MPIF FC-0208 powder metals to yield two 4.5 Kg (10 lb) lots of substantially homogeneous blends (#s 8 and 10) each containing 0.75% by weight of the EBS.

Two additional lots of the powder metals (each the same weight) are blended in the blender with equal parts by weight of Acumist® micronized polyolefin wax and cotton fibers to yield two blends (#s 9 and 11) each containing 0.75% by weight of the fiberlube. The Hall apparent density and flow rate of each blend in at least three samples is measured and averaged; the results are presented in Table 3 below:

TABLE 3

| Blend No. | Hall apparent density g/cc | Hall Flow Rate sec/50 g |
|---|---|---|
| 8 (F-0000 & EBS) | 3.12 | 28 |
| 9 (F-0000 & mod. lub.) | 3.04 | No Flow* |
| 10 (FC-0208 & EBS) | 3.03 | 35 |
| 11 (FC-0208 & mod. lub.) | 2.92 | No Flow* |

*the powder does not flow through the Hall funnel unless agitated ("No Flow" condition)

The No Flow condition of the samples made with fiber-lube may be the result of the blending procedure used, and changes in the procedure may be necessary to obtain flow. Note that the No Flow condition is not correlatable to flow obtained in a production facility where the delivery tube from a powder metal feed bin is typically at least 2.54 cm (1") in nominal diameter. Further, note that the apparent densities with the modified lubricant is 0.08–0.09 g/cc lower than with EBS, but not outside normal limits (2.90–3.20 g/cc) for F-0000; the apparent density of blend #9 is less than 3% lower than that of blend #8; and the apparent density of blend #11 is less than 4% lower than that of blend #10. Such small differences can typically be accommodated in a die cavity of a production press.

Each of the four blends is then used to make standard bars at pressures ranging from 2812 Kg/cm2 (20 TSI) to 8436 Kg/cm2 (60 TSI) which bars are tested for TRS, compressibility (green density), green strength, and sintered properties. All bars are then compacted into standard test bars under pressures ranging from 20 TSI to 60 TSI, and the bars are sintered in a sintering furnace equipped with a belt moving at 8.9 cm (3.5") per sec through zones having successively higher temperatures of to provide the desired time in the furnace's hot atmosphere of 97% $N_2$/3% $H_2$, the belt speed being in the range from 2.54 cm (1")/min to 30.5 cm (12")/min through four main temperature zones at 648.9° C. (1200° F.); 760° C. (1400° F.); 1121° C. (2050° F.); and 1121° C. (2050° F.). Measurements made on at least three samples, are averaged and recorded.

In the following Tables 4 and 5 are set forth comparative results obtained with the same F-0000 powder using identical amounts of lubricant (0.75% by weight), one being Acrawax® EBS, the other being a 50/50 combination of Acumist® polyolefin wax and micronized cotton fibers.

In the following Tables 6 and 7 are set forth comparative results obtained with the same FC-0208 powder using identical amounts of lubricant (0.75% by weight), one being Acrawax® EBS, the other being a 50/50 combination of Acumist® polyolefin wax and micronized cotton fibers.

TABLE 4

| MPIF F-0000 + 0.75% EBS | | | | | | | |
|---|---|---|---|---|---|---|---|
| Blend No. 8 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RF/H RB | Sintered DC, % from Die Size |
| 2812 (20 TSI) | 6.24 | 5.1 (741) | 669 (1475) | 6.23 | 271 (39.4) | H RF 22 | 0.00 |
| 4218 (30 TSI) | 6.71 | 9.96 (1447) | 1078 (2376) | 6.69 | 437.5 (63.5) | H RF 41 | 0.11 |
| 5624 (40 TSI) | 6.98 | 12.81 (1859) | 1324 (2919) | 6.98 | 569.8 (82.7) | H RF 63 | 0.16 |
| 7030 (50 TSI) | 7.15 | 14.99 (2176) | 1283 (2828) | 7.14 | 644.2 (93.5) | H RB 27 | 0.18 |
| 8436 (60 TSI) | 7.22 | 15.58 (2262) | 1360 (2998) | 7.22 | 670.4 (97.3) | H RB 33 | 0.21 |

10 tons/in² (TSI) = 1406.16 Kg/cm² pressure
Mpa refers to megapascals where 1 Mpa = 1000 KPa
Average stripping pressures range from (1125 lbf) @ 20 TSI to (1650) at 60 TSI

TABLE 5

| MPIF F-0000 + 0.75% (fibers + polyolefin wax) | | | | | | | |
|---|---|---|---|---|---|---|---|
| Blend No. 9 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RF/H RB | Sintered DC, % from Die Size |
| 2812 (20 TSI) | 6.17 | 6.8 (989) | 699 (1541) | 6.18 | 290.0 (42.1) | H RF 22 | −0.05 |
| 4218 (30 TSI) | 6.64 | 12.33 (1886) | 909 (2003) | 6.65 | 301.4 (62.6) | H RF 43 | 0.00 |
| 5624 (40 TSI) | 6.93 | 17.55 (2548) | 1206 (2659) | 6.95 | 483.6 (70.2) | H RF 47 | 0.04 |
| 7030 | 7.09 | 20.94 | 1453 | 7.13 | 553.9 | H RB 4 | 0.06 |

TABLE 5-continued

MPIF F-0000 + 0.75% (fibers + polyolefin wax)

| Blend No. 9 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RF/H RB | Sintered DC, % from Die Size |
|---|---|---|---|---|---|---|---|
| (50 TSI) | | (3040) | (3203) | | (80.4) | | |
| 8436 (60 TSI) | 7.21 | 17.05 (3241) | 1629 (3590) | 7.21 | 494.7 (71.8) | H RB 7 | 0.12 |

10 tons/in² (TSI) = 1406.16 Kg/cm² pressure
Mpa refers to megapascals where 1 Mpa = 1000 KPa

TABLE 6

MPIF FC-2008 + 0.75% BBS

| Blend No. 10 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RB | Sintered DC, % from Die Size |
|---|---|---|---|---|---|---|---|
| 2812 (20 TSI) | 6.29 | 5.13 (748) | 545.4 (1202) | 6.20 | 697.3 (101.2) | H RB 64 | 0.33 |
| 4218 (30 TSI) | 6.73 | 9.39 (1364) | 734.6 (1619) | 6.65 | 995.6 (144.5) | H RB 76 | 0.39 |
| 5624 (40 TSI) | 6.97 | 12.25 (1778) | 981.8 (2164) | 6.89 | 1199 (174.0) | H RB 84 | 0.45 |
| 7030 (50 TSI) | 7.08 | 13.60 (1974) | 1001 (2206) | 7.01 | 1252 (181.7) | H RB 88 | 0.48 |
| 8436 (60 TSI) | 7.13 | 13.60 (1974) | 1119 (2467) | 7.06 | 1343 (195.5) | H RB 89 | 0.51 |

10 tons/in² (TSI) = 1406.16 Kg/cm² pressure
Mpa refers to megapascals where 1 Mpa = 1000 KPa

TABLE 7

MPIF FC-2008 + 0.75% (fibers + polyolefin wax)

| Blend No. 11 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RB | Sintered DC, % from Die Size |
|---|---|---|---|---|---|---|---|
| 2812 (20 TSI) | 6.22 | 7.59 (1103) | 497.7 (1097) | 6.14 | 655.2 (95.1) | H RB 63 | 0.29 |
| 4218 (30 TSI) | 6.69 | 13.623 (1978) | 716.4 (1579) | 6.62 | 977.0 (141.8) | H RB 78 | 0.34 |
| 5624 (40 TSI) | 6.95 | 18.74 (2720) | 941.0 (2074) | 6.85 | 1154 (167.5) | H RB 85 | 0.41 |
| 7030 (50 TSI) | 7.08 | 21.07 (3058) | 931.0 (2052) | 6.99 | 1279 (185.7) | H RB 88 | 0.51 |
| 8436 (60 TSI) | 7.16 | 21.31 (3093) | 1081 (2383) | 7.06 | 1345 (195.2) | H RB 91 | 0.55 |

10 tons/in² (TSI) = 1406.16 Kg/cm² pressure
Mpa refers to megapascals where 1 Mpa = 1000 KPa
Avg. stripping pressures range from 408.3 Kgf (900 lbf) @ 2812 Kg/cm² (20 TSI) to 930.1 Kgf (2050 lbf) at Kg/cm2 (60 TSI)

It is evident from the results set forth in Tables 4–7 above that F-0000 bars made with modified lubricant have slightly lower compressibility than bars made with EBS, while those made with FC-02108 have substantially the same compressibility.

Bars of F-0000 made with modified lubricant have greatly increased green strength, 36% better on average than the green strength of bars made with EBS, irrespective of compaction pressure; and bars of F-0208 have 51% higher green strength. Such improvement in green strength ensures resistance to cracking under pressures of molding and ejecting a part; and to nicking, chipping and cracking of a part while being handles in the green state.

The peak ejection pressure, that is, the force required to initiate movement of a molded part out of the die cavity, is essentially the same for bars of blends #8 & #9 molded at typical molding pressures, but the force is higher for bars molded at more extreme pressures. For bars made from blends #10 & #11 however, the peak ejection pressures are substantially the same or lower irrespective of molding pressure.

The average stripping pressure, that is, the force required to keep the part moving out of the die cavity, is uniformly higher for each of the F-0000 bars, but either substantially the same or lower for bars of F-0208.

Bars of F-0000 made with modified lubricant have abnormally low growth relative to that of bars made with EBS, especially notable at extreme pressure; bars made with FC-0208 have normal sintered densities and dimensional change closely comparable to those of bars made with EBS.

TRS, which is obtained from a three point test carried out under controlled conditions on sintered bars to evaluate strength, for F-0000 bars made at lower pressures is normal but decreases for bars made at higher pressures; but for FC-0208 bars, the TRS values obtained for each lubricant are substantially similar.

The apparent hardness of F-0000 bars made with modified lubricant at the lower molding pressures is normal but decreases relative to the hardness of bars made with EBS at higher pressures; for F-0208 bars the apparent hardness is substantially the same for both lubricants at all molding pressures.

Examples 12–14

Evaluation of two compositions having different ratios and different amounts of a combination of micronized polyolefin wax lubricant ("wax") and micronized cotton fibers in a standard 316 stainless steel powder metal composition, one composition present in an amount of 1.0% by weight, the other 0.75% by weight:

To compare the effect of the fiberlube in blends #s 13 and 14 to the effect of a conventional, atomized Acrawax® EBS lubricant at 1% by weight (blend #12), each in Hoeganaes 316L powder the three blends are similarly prepared.

First, a small amount of the EBS lubricant is blended in a laboratory double cone blender with a lot of 316 L powder to yield a 0.907 Kg (2 lb) lot of a substantially homogeneous blend (#12) containing 1.0% by weight of the EBS.

Two additional lots of the 316 L powder (each the same weight) are blended in the blender to make blends #13 and #14. #13 contains 0.67% fibers/0.33 part by weight Acumist®; and, #14 contains 0.56% fibers with 0.19% Acumist® so blends #13 and #14 contain 1.0% and 0.75% by weight respectively of the fiberlube. The Hall apparent density and flow rate of each blend in at least three samples is measured and averaged; the results are presented in Table 8 below:

TABLE 8

| Blend No. | Hall apparent density g/cc | Hall Flow Rate sec/50 g |
|---|---|---|
| 12 (316L & 1% EBS) | 2.98 | No Flow* |
| 13 (316-L & 1% fiberlube) | 2.83 | No Flow* |
| 14 (316-L & 0.75% fiberlube) | 2.85 | 31 |

*the powder does not flow through the Hall funnel unless agitated.

It is evident that the apparent density of the blends with fiberlube is about 0.15 g/cc lower than that for the blend with the EBS. As pointed out earlier, such a slight difference in apparent density is tolerable in a production facility; if extreme precision is required, the die cavity may be made deeper. Note that the flow rate for blend #14 increases substantially with only a slight reduction in the fiberlube content.

Each of the three blends is then used to make standard bars at pressures ranging from 2812 Kg/cm2 (20 TSI) to 8436 Kg/cm2 (60 TSI) which bars are tested for TRS, compressibility (green strength) and sintered properties. All bars are then compacted into standard test bars under pressures ranging from 20 TSI to 60 TSI, and the bars are sintered in a sintering furnace equipped with a belt moving at 8.9 cm (3.5") per sec through zones having successively higher temperatures of to provide the desired time in the furnace's hot atmosphere of 100% H$_2$, the belt speed being 3.5"/min through four main temperature zones at 648.9° C. (1200° F.); 760° C. (1400° F.); 1287.8° C. (2350° F.); and 1287.8° C. (2350° F.). Measurements made on at least three samples, are averaged and recorded.

In the following Tables 9, 10 and 11 are set forth comparative results obtained with each of the blends #s 12, 13 and 14.

TABLE 9

| | 316-L + 1.0% EBS | | | | | | |
|---|---|---|---|---|---|---|---|
| Blend No. 12 @ Kg/cm$^2$ (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RB | Sintered DC, % from Die Size |
| 2812 (20 TSI) | 5.71 | 2.956 (429) | 370.7 (817) | 5.92 | 444.4 (64.5) | H RB 13 | −1.23 |
| 4218 (30 TSI) | 6.16 | 6.139 (891) | 618.9 (1364) | 6.37 | 607.0 (88.1) | H RB 37 | −1.07 |
| 5624 (40 TSI) | 6.48 | 9.494 (1378) | 844.8 (1862) | 6.68 | 746.2 (108.3 | H RB 50 | −0.97 |
| 7030 (50 TSI) | 6.69 | 12.464 (1809) | 1089.8 (2402) | 6.90 | 876.4 (127.2) | H RB 59 | −0.87 |
| 8436 (60 TSI) | 6.87 | 14.89 (2161) | 1368.9 (3017) | 7.07 | 975.6 (141.6) | H RB 65 | −0.78 |

10 tons/in$^2$ (TSI) = 1406.16 Kg/cm$^2$ pressure
Mpa refers to megapascals where 1 Mpa = 1000 KPa

TABLE 10

316-L + 1.0% fiberlube

| Blend No. 13 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness H RB | Sintered DC, % from Die Size |
|---|---|---|---|---|---|---|---|
| 2812 (20 TSI) | 5.71 | 2.956 (897) | 370.7 (967) | 5.75 | 444.4 (57.7) | H RB 5 | −1.20 |
| 4218 (30 TSI) | 6.16 | 6.139 (1728) | 618.9 (1485) | 6.22 | 607.0 (81.4) | H RB 30 | −1.08 |
| 5624 (40 TSI) | 6.48 | 9.494 (2719) | 844.8 (2093) | 6.55 | 746.2 (102.9) | H RB 44 | −0.95 |
| 7030 (50 TSI) | 6.69 | 12.464 (3674) | 1089.8 (2548) | 6.78 | 876.4 (117.7) | H RB 54 | −0.85 |
| 8436 (60 TSI) | 6.87 | 14.89 (4410) | 1368.9 (3044) | 6.96 | 975.6 (134.3) | H RB 62 | −0.78 |

10 tons/in² (TSI) = 1406.16 Kg/cm² pressure
Mpa refers to megapascals where 1 Mpa = 1000 KPa

TABLE 11

316-L + 0.75% fiberlube

| Blend No. 14 @ Kg/cm² (TSI) | Green Density g/cc | Green Strength MPa (psi) | Peak Ejection Pressure Kgf (lbf) | Sintered Density, g/cc | Sintered TRS MPa (Ksi) | Sintered Apparent Hardness HRB | Sintered DC, % from Die Size |
|---|---|---|---|---|---|---|---|
| 2812 (20 TSI) | 5.71 | 6.159 (894) | 451.4 (995) | 5.76 | 407.2 (59.1) | H RB 6 | −1.22 |
| 4218 (30 TSI) | 6.16 | 11.79 (1712) | 771.3 (1678) | 6.22 | 558.8 (81.1) | H RB 30 | −1.07 |
| 5624 (40 TSI) | 6.48 | 17.98 (2609) | 968.2 (2134) | 6.57 | 716.6 (104.0) | H RB 46 | −0.96 |
| 7030 (50 TSI) | 6.69 | 23.65 (3433) | 1203.7 (2653) | 6.81 | 825.4 (119.8) | H RB 55 | −0.87 |
| 8436 (60 TSI) | 6.87 | 29.89 (4338) | 1502.7 (3312) | 6.99 | 947.4 (137.5) | H RB 62 | −0.79 |

10 tons/in² (TSI) = 1406.16 Kg/cm² pressure
Mpa refers to megapascals where 1 Mpa = 1000 KPa Note the surprisingly high green strength of the blends containing fiberlube, irrespective of molding pressure.

It is also evident from the foregoing data that the compresibility of the blends with fiberlube is typically about 0.15 g/cc lower than that for the blend with EBS; the reduction in the fiberlube content to 0.75% showed improvement in green density at the higher pressures. The difference in peak ejection pressures is not significant in a production facility. The sintered density of the bars corresponded generally with the differences in green density. The percent shrinkage in dimensional change was less for the blends containing fiberlube, at the same density, compared to the blend with EBS; and TRS and apparent hardness for bars having the same sintered density are substantially the same.

Having thus provided a general disclosure of the relevant subject matter and described the novel modified lubricant and powder metal mixtures in detail, and illustrated the invention with specific embodiments of the best mode of making and using the invention, it is to be understood that no undue restrictions are to be imposed by reason of the specific embodiment illustrated and described, and particularly, that the invention is not restricted to a slavish adherence to the details set forth herein.

What is claimed is:

1. A powder metal composition comprising a ferrous metal powder and a modified lubricant consisting essentially of a lubricant powder and comminuted cellulose fibers having an average length less than 70 μm and a diameter in the range from about 1μ to 20μ, the modified lubricant being present in an amount less than 2% by weight of the composition, the mixture having (i) a Hall apparent density numerically no smaller than 10% less than that obtained for the same powder metal mixture made with a conventional lubricant without the cellulose fibers, and (ii) a Hall flow rate which is at least 25 sec/50 g of mixture.

2. The composition of claim 1 wherein the lubricant powder is selected from the group consisting of fatty acid monoamides, fatty acid bisamides, metal soaps and polyolefin waxes.

3. The composition of claim 1 wherein the comminuted cellulose fibers have an average length in the range from about 1μ but less than 70μ and a Hall apparent density in the range from 2.7 to 3.5 g/cc.

4. In a powder ferrous metal mixture including a modified lubricant consisting essentially of a lubricant powder and cellulose fibers the mixture having an Hall flow rate of less than 25 sec/50 g of mixture, the improvement comprising comminuted cellulose fibers having an average length in the range from about 1μ but less than 70μ and a diameter in the range from about 1μ to 20μ, the lubricant and fibers together present in an amount less than 2% by weight of the powder metal mixture, the ratio of lubricant/fibers being in the range from 1:2 to 10:1.

5. A method for making a homogeneous ferrous powder metal mixture comprising,
- combining metal particles having an average particle diameter smaller than about 70 μm with a modified lubricant consisting essentially of a lubricant and comminuted cellulose fibers together present in an amount less than 2% by weight of the mixture, the lubricant having an average particle equivalent diameter smaller than 50 μm, the cellulose fibers having an average length smaller than 70 μm; and,
- mixing the mixture for a time sufficient to yield specifications of (i) Hall apparent density numerically no smaller than 10% less than that obtained for the same powder metal mixture made with a conventional lubricant without the cellulose fibers, and (ii) Hall flow rate which is at least 25 sec/50 g of mixture.

6. The method of claim 5 wherein the Hall apparent density is greater than that obtained for the same powder metal mixture made with a conventional lubricant without the cellulose fibers.

7. A modified lubricant adapted for use in a powder metal article, the modified lubricant consisting essentially of a lubricant selected from the group consisting of an inorganic compound, an organometal compound, and a wax, the lubricant having an average particle diameter smaller than 50 μm, in combination with comminuted cellulose fibers having an average length smaller than 70 μm, the weight ratio of lubricant to fibers being in the range from about 1:2 to 10:1.

* * * * *